(12) United States Patent
Chen et al.

(10) Patent No.: US 9,527,801 B2
(45) Date of Patent: Dec. 27, 2016

(54) PROCESS AND DEVICE FOR RECYCLING WASTE ACID PRODUCED IN PROCESS OF PRODUCING ZOALENE

(71) Applicant: Zhejiang Rongyao Biotech CO., LTD., Linhai, Zhejiang (CN)

(72) Inventors: Rener Chen, Zhejiang (CN); Fei Shi, Zhejiang (CN); Jianhua Chen, Zhejiang (CN); Na Zhang, Zhejiang (CN)

(73) Assignee: ZHEJIANG RONGYAO BIOTECH CO., LTD., Linhai, Zhejiang (CN)

( * ) Notice: Subject to any disclaimer, the term of this patent is extended or adjusted under 35 U.S.C. 154(b) by 0 days.

(21) Appl. No.: 14/978,556

(22) Filed: Dec. 22, 2015

(65) Prior Publication Data

US 2016/0185711 A1 Jun. 30, 2016

(30) Foreign Application Priority Data

Dec. 24, 2014 (CN) .......................... 2014 1 0809757

(51) Int. Cl.
| | | |
|---|---|---|
| *C07C 231/02* | (2006.01) | |
| *C07C 201/08* | (2006.01) | |
| *C07C 201/12* | (2006.01) | |
| *B01J 19/18* | (2006.01) | |
| *C01B 17/94* | (2006.01) | |

(52) U.S. Cl.
CPC ............. *C07C 231/02* (2013.01); *C01B 17/94* (2013.01); *C07C 201/08* (2013.01); *C07C 201/12* (2013.01)

(58) Field of Classification Search
CPC .... C07C 231/02; C07C 201/08; C07C 231/12; C01B 17/94
See application file for complete search history.

(56) References Cited

FOREIGN PATENT DOCUMENTS

| | | | |
|---|---|---|---|
| CN | 101165043 | * | 4/2008 |
| CN | 104211600 | * | 12/2014 |

OTHER PUBLICATIONS

McGookin et al, J. of the Soc. of Chemical Industry, 1940, 59, 92-4(abstract only).*

* cited by examiner

*Primary Examiner* — Shailendra Kumar
(74) *Attorney, Agent, or Firm* — Global IP Services; Tianhua Gu

(57) ABSTRACT

A process and a device for recycling waste acid produced in the process of producing Zoalene. The process comprises steps: heating, depressurizing and distilling the waste acid recycled after nitration reaction; collecting acid liquid A and distilled water A; mixing the acid liquid A with new concentrated sulfuric acid in proportion, and putting the mixture to a new Zoalene nitration reaction process; and putting the distilled water A into a diluting pot for diluting the liquid produced in the nitration reaction. The waste acid produced in the process of producing Zoalene is recycled and not directly discharged; water resources are recycled, waste of the water resources is reduced, and discharge of waste water produced in the process of producing Zoalene is greatly reduced, so that not only production cost is saved, but also environment pressure is reduced.

9 Claims, 1 Drawing Sheet

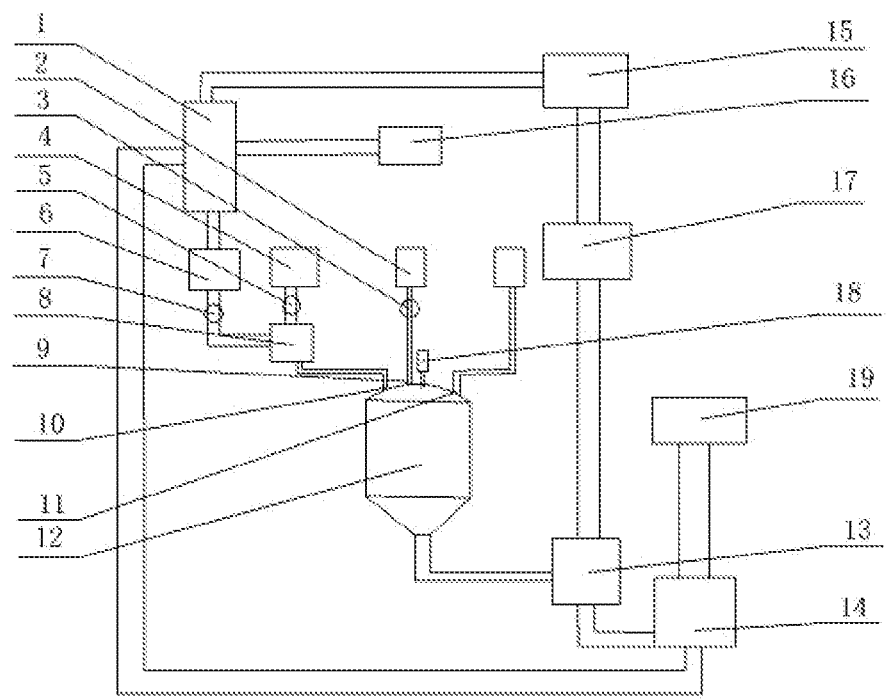

PROCESS AND DEVICE FOR RECYCLING WASTE ACID PRODUCED IN PROCESS OF PRODUCING ZOALENE

TECHNICAL FIELD the invention belongs to the technical field of treating waste acid and relates to a process for recycling the waste acid, in particularly to a process and a device for recycling the waste acid produced in the process of producing Zoalene.

BACKGROUND ART

Zoalene (chemical name is called 3,5-dinitro-2-methyl-benzoic acid) is a fairly ideal drug which is characterized of broad spectrum, efficacy, low toxicity, stable performances, small drug resistance, no residue and no influence on immunity of poultry. The product can promote the growth of chooks, if used in feeds, and it is effective against all *eimeria tenella*, such as *eimeria tenella, eimeria necatrix, eimeria brunetti, eimeria acervulina* and *eimeria maxima*, and effective against coccidium of turkeys, particularly against the *eimeria tenella* and the *eimeria necatrix*. The action mechanism of Zoalene is mainly to inhibit fission gemmas without sexual cycles and mainly acted on sporozoites and the first generation of agamonts. The product is not only used for prevention, but also used for treating; the applied curative dose does not have harmful effect on growth and development of the chooks and hatching rate of eggs, and have effects in good prevention on coccidiosis of rabbits; therefore, Zoalene is a good anti-considiosis medicament.

In traditional Zoalene producing methods, ortho-toluic acid is mainly adopted as a starting material, and three synthetic routes are usually used; the first route comprises the steps of nitrating the ortho-toluic acid to obtain the 3,5-dinitro-2-methylbenzoic acid, chloridizing the 3,5-dinitro-2-methylbenzoic acid to obtain acyl chloride, and carry out aminolysis action to obtain Zoalene; the second route comprises the steps of making the ortho-toluic acid into the ortho-methyl benzamide and nitrating ortho-methyl benzamide to obtain Zoalene; and the third route comprises the step of carrying out aminolysis action to obtain Zoalene. At present, the first route is the main preparation method of Zoalene because of high product yield, but in the method, a large amount of concentrated sulfuric acid and concentrated nitric acid are needed in the nitration reaction; after reacted, a large amount of waste acid is produced, and the waste acid has large acid content and sulfuric acid. The traditional waste acid treating method mainly adopts neutralization reaction, but a large amount of lime and alkali in are needed in the neutralization reaction, and costs for solid sedimentation treatment of the neutralizing product such as calcium sulfate are increased. If the waste acid is directly discharged to environment, water or soil will be acidized and ecological environment will be damaged. Therefore, if a recycling process and device can be designed for recycling the waste acid produced in the nitration reaction of the ortho-toluic acid and reusing in the reaction, the wastewater treating costs of the production process can be reduced, environment pollution can be greatly reduced, which is significant in protecting environment against pollution.

Invention Content

To solve the problem that a large amount of waste acid produced in the nitration reaction during the process of producing Zoalene pollutes the environment, the invention provides a process for recycling the waste acid produced in the process of producing the Zoalene; in the method, the concentrated sulfuric acid with a few organics is separated from water by treating the waste acid, and the recycled concentrated sulfuric acid is reused in the production process, so that the environment pollution is reduced and costs are saved; the water is applied to the production process, so that the water resources can be recycled.

On the other hand, the invention provides a device for recycling the waste acid produced in the process of producing Zoalene to realize the recycling process.

The technical scheme used in the invention is as follows: a process for recycling waste acid produced in the process of producing Zoalene, comprising a nitration process, a chlorination process and an ammonization process, wherein the nitration process comprises the following steps: putting concentrated sulfuric acid into an enamel reactor, starting a mixer, putting in ortho-toluic acid and mixing it until completely dissolved, adding nitric acid to the system, controlling the system temperature at 90-100 DEG. C., continuously mixing to react for 0.5-1.5 h after added, and then cooling; diluting the liquid with distilled water, then filtering, and then washing and drying the solid to obtain a nitration product 3,5-dinitro-2-methylbenzoic acid; putting the waste acid which is diluted and washed in the nitration process into a distillation tower, later heating, depressurizing and distilling; setting the vacuum degree for depressurizing and distilling the water acid at 0.07-0.1 MPa, putting the acid liquid A obtained by distillation and concentration into a mixing tank, and adding new concentrated sulfuric acid to the mixing tank, wherein the mass ratio of the acid liquid A to the new concentrated sulfuric acid mixed above is 1-5:1; after mixing, putting the mixed sulfuric acid to a reactor to carry out a new nitration reaction; recycling and putting the distilled water A which is obtained by heating, depressurizing and distilling into a condenser for cooling, storing the cooled distilled water A in a recycled water storage tank, and putting the distilled water A to a diluting pot to dilute the 3,5-dinitro-2-methylbenzoic acid produced in the new nitration process. The recycled waste acid contains sulfuric acid, nitric acid, water and ortho-toluic acid. From a sufficient amount of experimentation, if the acid liquid A recycled after distilled is mixed with new concentrated sulfuric acid in certain proportion under different conditions, influences on the product yield and content are different, and the product yield and content obtained in the conditions of the invention are equivalent to that obtained in the production carried out with new concentrated sulfuric acid; therefore, based on guarantee of product quality in the invention, the waste acid produced in the production process can be fully used; the recycled distilled water A contain little nitric acid, so that the distilled water A can be used for diluting in the diluting pot, and the product cannot be influenced.

For the process for recycling the waste acid produced in the process of producing the Zoalene, the starting temperature to heat the waste acid is 50-120 DEG C., and the temperature to stop depressurizing and distilling the waste acid is 135-180 DEG C.

As the preferable measure in the invention, for the process for recycling the waste acid produced in the process of producing the Zoalene, the starting temperature to heat the waste acid is 90-110 DEG C., and the temperature to stop depressurizing and distilling the waste acid is 150-170 DEG C.

As the preferable measure in the invention, for the process for recycling the waste acid produced in the process of producing the Zoalene, the waste acid A and the new concentrated sulfuric acid are mixed and put in proportion of 2 to 3:1 by weight.

For the process for recycling the waste acid produced in the process of producing the Zoalene, the input rate of the added ortho-toluic acid:nitric acid:concentrated sulfuric acid is set as 1:2-3:5-18.

For the process for recycling the waste acid produced in the process of producing the Zoalene, the input rate of the added ortho-toluic acid:nitric acid:concentrated sulfuric acid is set as 1:2.2-2.6:8-12.

For the process for recycling the waste acid produced in the process of producing the Zoalene, the dropping time of the nitric acid is 0.5-2 h.

The invention further provides a device for recycling the waste acid produced in the process of producing the Zoalene, comprising an enamel reactor, wherein a mixer is arranged in the enamel reactor, the enamel reactor is provided with a nitric acid inlet, a sulfuric acid inlet and an ortho-toluic acid inlet, wherein the outlet of the enamel reactor is connected with a diluting pot, and the diluting pot is connected with a filtering slot; the waste acid outlet is connected with the distillation tower, the distillation tower is connected with a vacuum pump, the acid liquid A outlet of the distillation tower is connected with an acid liquid A storage tank, the acid liquid A storage tank is connected with the inlet of a blending tank, the blending tank is further connected with a concentrated sulfuric acid storage tank, the outlet of the blending tank is connected with the sulfuric acid inlet of the enamel reactor, the distilled water outlet of the distillation tower is connected with a condenser, the outlet of the condenser is connected with a recycled water storage tank, and the outlet of the recycled water storage tank is connected with the diluting pot.

As the further improving measure in the invention, for the device, a metering pump I is arranged between a nitric acid storage tank and the enamel reactor, a metering pump II is arranged between the concentrated sulfuric acid storage tank and the blending tank, and a metering pump III is arranged between the acid liquid A storage tank and the blending tank.

Compared with prior art, the invention mainly has the following beneficial effects: by recycling the waste acid produced in the process of producing Zoalene in a way of heating, depressurizing and concentrating the waste acid and reusing the waste acid in the nitration reaction, the waste acid is recycled, the use ratio of the concentrated sulfuric acid is improved, the discharged wastewater does not contain the waste acid while the costs are reduced, and the environmental-friendly production process without pollution is realized; by reusing the distilled water produced when the waste acid is depressurized, distilled and concentrated in the dilution process of the nitration products, the water resources are recycled, the waste of the water resources is reduced, and the discharge of waste water produced in the process of producing the Zoalene is greatly reduced, so that not only production cost is saved, but also environment pressure is reduced; the method is simple in separation process, feasible in recycling method, high in yield, simple to operate and significant of great significance to environment protection.

DESCRIPTION WITH FIGURE

The invention is described with a FIGURE.

FIG. 1 is the structure sketch of the device in the invention.

Description of marks on the FIGURE: 1-distillation tower, 2-nitric acid storage tank, 3-metering pump I, 4-sulfuric acid storage tank, 5-metering pump II, 6-acid liquid A storage tank, 7-metering pump III, 8-blending tank, 9-nitric acid inlet, 10-sulfuric acid inlet, 11-ortho-toluic acid inlet, 12-enamel reactor, 13-diluting pot, 14-filtering tank, 15-condenser, 16-vacuum pump, 17-recycled water storage tank, 18-mixer, 19-water storage tank.

SPECIFIC EMBODIMENTS

Embodiment 1

Adding 3000 kg of the recycled waste acid into the 5000 L distillation tower 1, wherein the tested sulfuric acid content is 31.5%; when ready, starting to mix, rising the temperature to 50 DEG C., starting the vacuum pump to vacuumize for 16, keeping the vacuum degree at 0.07 MPa, and collecting the distilled water, wherein the temperature is risen gradually in the distilling process; stopping to distill at 150 DEG C.; recycling the sulfuric acid, adding the cooled sulfuric acid into the acid liquid A storage tank 6 to obtain the 1125 kg of the acid liquid, wherein the tested content of the sulfuric acid in the acid liquid A is 84%; putting the distilled water A obtained by distilling into the condenser 15 to cool, storing the cooled distilled water A in the recycled water storage tank 17, and then putting the cooled distilled water in the diluting pot 13; putting all the recycled acid liquid A into the blending tank 8 through the metering pump III 7, and putting 350 kg of new concentrated sulfuric acid which is stored in the sulfuric acid storage tank 4 into the blending tank 8 through the metering pump II 5; after blended, putting the mixture into the 2000 L enamel reactor 12, then starting the mixer 18, and then putting 136 kg of the ortho-toluic acid; after fully blended, adding 151 kg of the concentrated nitric acid which is stored in the nitric acid storage tank 2 through the metering pump I 3, wherein the concentrated nitric acid is completely added within one hour by controlling the adding speed and the reaction temperature is controlled at 90 DEG C.; keeping the reaction temperature for 1 h after the concentrated nitric acid is added completely; putting the cooled mixture into the diluting pot 13 in which 1500 kg of the recycled water is placed, and then mixing to dilute; putting the fully cooled liquid into the filtering tank 14 to be filtered, washing the filtered solid with the clean water stored in the water storage tank 19, later taking the product from the filtering tank, and then drying the product to obtain 187.6 kg of 3,5-dinitro-2-methylbenzoic acid, wherein the yield is 83% and the content is 91%; putting the collected waste acid and the washing liquid to the distillation tower 1 into the cyclic process for recycling.

Embodiment 2

Adding 3000 kg of the recycled waste acid into the 5000 L distillation tower 1, wherein the tested sulfuric acid content is 35%; when ready, starting to mix, rising the temperature to 50 DEG C., starting the vacuum pump to vacuumize for 16, keeping the vacuum degree at 0.1 MPa, and collecting the distilled water, wherein the temperature is risen gradually in the distilling process; stopping to distill at 155 DEG C.; recycling the sulfuric acid, adding the cooled sulfuric acid into the acid liquid A storage tank 6 to obtain the 1180 kg of the acid liquid, wherein the tested content of the sulfuric acid in the acid liquid A is 89%; putting the distilled water A obtained by distilling into the condenser 15 to cool, storing the cooled distilled water A in the recycled water storage tank 17, and then putting the cooled distilled water in the diluting pot 13; putting all the recycled acid liquid A into the blending tank 8 through the metering pump III 7, and putting 250 kg of new concentrated sulfuric acid which is stored in the sulfuric acid storage tank 4 into the blending tank 8 through the metering pump II 5; after blended, putting the mixture into the 2000 L enamel reactor 12, then starting the mixer 18, and then putting 217 kg of the ortho-toluic acid; after fully blended, adding 232 kg of the concentrated nitric acid which is stored in the nitric acid storage tank 2 through the metering pump I 3, wherein the concentrated nitric acid is completely added within one hour by controlling the adding speed and the reaction temperature is controlled at 95 DEG C.; keeping the reaction temperature for 1.2 h after the concentrated nitric acid is added completely; putting the cooled mixture into the diluting pot 13 in which 1600 kg of the recycled water is placed, and then mixing to dilute; putting the fully cooled liquid into the filtering tank 14 to be filtered, washing the filtered solid with the clean water stored in the water storage tank 19, later taking the product from the filtering tank, and then drying the product to obtain 343 kg of 3,5-dinitro-2-methylbenzoic acid, wherein the yield is 95% and the content is 93%; putting the collected waste acid and the washing liquid to the distillation tower 1 into the cyclic process for recycling.

Embodiment 3

Adding 2800 kg of the recycled waste acid into the 5000 L distillation tower 1, wherein the tested sulfuric acid content is 32%; when ready, starting to mix, rising the temperature to 90 DEG C., starting the vacuum pump to vacuumize for 16, keeping the vacuum degree at 0.08 MPa, and collecting the distilled water, wherein the temperature is risen gradually in the distilling process; stopping to distill at 160 DEG C.; recycling the sulfuric acid, adding the cooled sulfuric acid into the acid liquid A storage tank 6 to obtain the 966 kg of the acid liquid, wherein the tested content of the sulfuric acid in the acid liquid A is 92.8%; putting the distilled water A obtained by distilling into the condenser 15 to cool, storing the cooled distilled water A in the recycled water storage tank 17, and then putting the cooled distilled water in the diluting pot 13; putting all the recycled acid liquid A into the blending tank 8 through the metering pump III 7, and putting 350 kg of new concentrated sulfuric acid which is stored in the sulfuric acid storage tank 4 into the blending tank 8 through the metering pump II 5; after blended, putting the mixture into the 2000 L enamel reactor 12, then starting the mixer 18, and then putting 217 kg of the ortho-toluic acid; after fully blended, adding 248 kg of the concentrated nitric acid which is stored in the nitric acid storage tank 2 through the metering pump I 3, wherein the concentrated nitric acid is completely added within one hour by controlling the adding speed and the reaction temperature is controlled at 96 DEG C.; keeping the reaction temperature for 1.2 h after the concentrated nitric acid is added completely; putting the cooled mixture into the diluting pot 13 in which 1600 kg of the recycled water is placed, and then mixing to dilute; putting the fully cooled liquid into the filtering tank 14 to be filtered, washing the filtered solid with the clean water stored in the water storage tank 19, later taking the product from the filtering tank, and then drying the product to obtain 347 kg of 3,5-dinitro-2-methylbenzoic acid, wherein the yield is 94.6% and the content is 97.9%; putting the collected waste acid and the washing liquid to the distillation tower 1 into the cyclic process for recycling.

Embodiment 4

Adding 3000 kg of the recycled waste acid into the 5000 L distillation tower 1, wherein the tested sulfuric acid content is 30%; when ready, starting to mix, rising the temperature to 95 DEG C., starting the vacuum pump to vacuumize for 16, keeping the vacuum degree at 0.1 MPa, and collecting the distilled water, wherein the temperature is risen gradually in the distilling process; stopping to distill at 170 DEG C.; recycling the sulfuric acid, adding the cooled sulfuric acid into the acid liquid A storage tank 6 to obtain the 947 kg of the acid liquid, wherein the tested content of the sulfuric acid in the acid liquid A is 95%; putting the distilled water A obtained by distilling into the condenser 15 to cool, storing the cooled distilled water A in the recycled water storage tank 17, and then putting the cooled distilled water in the diluting pot 13; putting all the recycled acid liquid A into the blending tank 8 through the metering pump III 7, and putting 270 kg of new concentrated sulfuric acid which is stored in the sulfuric acid storage tank 4 into the blending tank 8 through the metering pump II 5; after blended, putting the mixture into the 2000 L enamel reactor 12, then starting the mixer 18, and then putting 200 kg of the ortho-toluic acid; after fully blended, adding 221 kg of the concentrated nitric acid which is stored in the nitric acid storage tank 2 through the metering pump I 3, wherein the concentrated nitric acid is completely added within 1.2 h by controlling the adding speed and the reaction temperature is controlled at 95 DEG C.; keeping the reaction temperature for 50 min after the concentrated nitric acid is added completely; putting the cooled mixture into the diluting pot 13 in which 1560 kg of the recycled water is placed, and then mixing to dilute; putting the fully cooled liquid into the filtering tank 14 to be filtered, washing the filtered solid with the clean water stored in the water storage tank 19, later taking the product from the filtering tank, and then drying the product to obtain 316 kg of 3,5-dinitro-2-methylbenzoic acid, wherein the yield is 95% and the content is 98.1%; putting the collected waste acid and the washing liquid to the distillation tower 1 into the cyclic process for recycling.

Embodiment 5

Adding 2800 kg of the recycled waste acid into the 5000 L distillation tower 1, wherein the tested sulfuric acid content is 30%; when ready, starting to mix, rising the temperature to 110 DEG C., starting the vacuum pump to vacuumize for 16, keeping the vacuum degree at 0.08 MPa, and collecting the distilled water, wherein the temperature is risen gradually in the distilling process; stopping to distill at 180 DEG C.; recycling the sulfuric acid, adding the cooled sulfuric acid into the acid liquid A storage tank 6 to obtain the 896 kg of the acid liquid, wherein the tested content of the sulfuric acid in the acid liquid A is 93.8%; putting the distilled water A obtained by distilling into the condenser 15 to cool, storing the cooled distilled water A in the recycled water storage tank 17, and then putting the cooled distilled water in the diluting pot 13; putting all the recycled acid liquid A into the blending tank 8 through the metering pump III 7, and putting 336 kg of new concentrated sulfuric acid which is stored in the sulfuric acid storage tank 4 into the blending tank 8 through the metering pump II 5; after blended, putting the mixture into the 2000 L enamel reactor 12, then starting the mixer 18, and then putting 136 kg of the ortho-toluic acid; after fully blended, adding 158 kg of the concentrated nitric acid which is stored in the nitric acid storage tank 2 through the metering pump I 3, wherein the concentrated nitric acid is completely added within 45 min by controlling the adding speed and the reaction temperature is controlled at 98 DEG C.; keeping the reaction temperature for 40 min after the concentrated nitric acid is added completely; putting the cooled mixture into the diluting pot 13 in which 1600 kg of the recycled water is placed, and then mixing to dilute; putting the fully cooled liquid into the filtering tank 14 to be filtered, washing the filtered solid with the clean water stored in the water storage tank 19, later taking the product from the filtering tank, and then drying the product to obtain 197.4 kg of 3,5-dinitro-2-methylbenzoic acid, wherein the yield is 94% and the content is 98.5%; putting the collected waste acid and the washing liquid to the distillation tower 45 into the cyclic process for recycling.

Embodiment 6

Adding 3000 kg of the recycled waste acid into the 5000 L distillation tower 1, wherein the tested sulfuric acid content is 29.5%; when ready, starting to mix, rising the temperature to 100 DEG C., starting the vacuum pump to vacuumize for 16, keeping the vacuum degree at 0.09 MPa, and collecting the distilled water, wherein the temperature is risen gradually in the distilling process; stopping to distill at 170 DEG C.; recycling the sulfuric acid, adding the cooled sulfuric acid into the acid liquid A storage tank 6 to obtain the 940 kg of the acid liquid, wherein the tested content of the sulfuric acid in the acid liquid A is 94.1%; putting the distilled water A obtained by distilling into the condenser 15 to cool, storing the cooled distilled water A in the recycled water storage tank 17, and then putting the cooled distilled water in the diluting pot 13; putting all the recycled acid liquid A into the blending tank 8 through the metering pump III 7, and putting 880 kg of new concentrated sulfuric acid which is stored in the sulfuric acid storage tank 4 into the blending tank 8 through the metering pump II 5; after blended, putting the mixture into the 2000 L enamel reactor 12, then starting the mixer 18, and then putting 136 kg of the ortho-toluic acid; after fully blended, adding 189 kg of the concentrated nitric acid which is stored in the nitric acid storage tank 2 through the metering pump I 3, wherein the concentrated nitric acid is completely added within 1.2 h by controlling the adding speed and the reaction temperature is controlled at 96 DEG C.; keeping the reaction temperature for 60 min after the concentrated nitric acid is added completely; putting the cooled mixture into the diluting pot 13 in which 1750 kg of the recycled water is placed, and then mixing to dilute; putting the fully cooled liquid into the filtering tank 14 to be filtered, washing the filtered solid with the clean water stored in the water storage tank 19, later taking the product from the filtering tank, and then drying the product to obtain 214 kg of 3,5-dinitro-2-methylbenzoic acid, wherein the yield is 94.9% and the content is 98.3%; putting the collected waste acid and the washing liquid to the distillation tower 1 into the cyclic process for recycling.

Embodiment 7

Adding 3000 kg of the recycled waste acid into the 5000 L distillation tower 1, wherein the tested sulfuric acid content is 28%; when ready, starting to mix, rising the temperature to 120 DEG C., starting the vacuum pump to vacuumize for 16, keeping the vacuum degree at 0.08 MPa, and collecting the distilled water, wherein the temperature is risen gradually in the distilling process; stopping to distill at 158 DEG C.; recycling the sulfuric acid, adding the cooled sulfuric acid into the acid liquid A storage tank 6 to obtain the 1097 kg of the acid liquid, wherein the tested content of the sulfuric acid in the acid liquid A is 89.3%; putting the distilled water A obtained by distilling into the condenser 15 to cool, storing the cooled distilled water A in the recycled water storage tank 17, and then putting the cooled distilled water in the diluting pot 13; putting all the recycled acid liquid A into the blending tank 8 through the metering pump III 7, and putting 300 kg of new concentrated sulfuric acid which is stored in the sulfuric acid storage tank 4 into the blending tank 8 through the metering pump II 5; after blended, putting the mixture into the 2000 L enamel reactor 12, then starting the mixer 18, and then putting 136 kg of the ortho-toluic acid; after fully blended, adding 164 kg of the concentrated nitric acid which is stored in the nitric acid storage tank 2 through the metering pump I 3, wherein the concentrated nitric acid is completely added within 1.2 h by controlling the adding speed and the reaction temperature is controlled at 100 DEG C.; keeping the reaction temperature for 50 min after the concentrated nitric acid is added completely; putting the cooled mixture into the diluting pot 13 in which 1700 kg of the recycled water is placed, and then mixing to dilute; putting the fully cooled liquid into the filtering tank 14 to be filtered, washing the filtered solid with the clean water stored in the water storage tank 19, later taking the product from the filtering tank, and then drying the product to obtain 201 kg of 3,5-dinitro-2-methylbenzoic acid, wherein the yield is 89% and the content is 94.3%; putting the collected waste acid and the washing liquid to the distillation tower 1 into the cyclic process for recycling.

Embodiment 8

Adding 3100 kg of the recycled waste acid into the 5000 L distillation tower 1, wherein the tested sulfuric acid content is 31.6%; when ready, starting to mix, rising the temperature to 115 DEG C., starting the vacuum pump to vacuumize for 16, keeping the vacuum degree at 0.07 MPa, and collecting the distilled water, wherein the temperature is risen gradually in the distilling process; stopping to distill at 170 DEG C.; recycling the sulfuric acid, adding the cooled sulfuric acid into the acid liquid A storage tank 6 to obtain the 1148 kg of the acid liquid, wherein the tested content of the sulfuric acid in the acid liquid A is 85.3%; putting the distilled water A obtained by distilling into the condenser 15 to cool, storing the cooled distilled water A in the recycled water storage tank 17, and then putting the cooled distilled water in the diluting pot 13; putting all the recycled acid liquid A into the blending tank 8 through the metering pump III 7, and putting 650 kg of new concentrated sulfuric acid which is stored in the sulfuric acid storage tank 4 into the blending tank 8 through the metering pump II 5; after blended, putting the mixture into the 2000 L enamel reactor 12, then starting the mixer 18, and then putting 231 kg of the ortho-toluic acid; after fully blended, adding 236 kg of the concentrated nitric acid which is stored in the nitric acid storage tank 2 through the metering pump I 3, wherein the concentrated nitric acid is completely added within 1.5 h by controlling the adding speed and the reaction temperature is controlled at 92 DEG C.; keeping the reaction temperature for 80 min after the concentrated nitric acid is added completely; putting the cooled mixture into the diluting pot 13 in which 1800 kg of the recycled water is placed, and then mixing to dilute; putting the fully cooled liquid into the filtering tank 14 to be filtered, washing the filtered solid with the clean water stored in the water storage tank 19, later taking the product from the filtering tank, and then drying the product to obtain 334 kg of 3,5-dinitro-2-methylbenzoic acid, wherein the yield is 87% and the content is 91.3%; putting the collected waste acid and the washing liquid to the distillation tower 1 into the cyclic process for recycling.

Comparison 1

Adding 600 kg of the concentrated sulfuric acid in the 1000 L enamel reactor 12, starting the mixer 18, and then putting 100 kg of the ortho-toluic acid; after fully blended, adding 120 kg of the concentrated nitric acid, wherein the concentrated nitric acid completely added within 1 h by controlling the adding speed and the reaction temperature is controlled at not more than 100 DEG C.; keeping the reaction temperature for 60 min after the concentrated nitric acid is added completely; putting the cooled mixture into the diluting pot 13 in which 1200 kg of the recycled water is placed, and then mixing to dilute; filtering the fully cooled liquid, washing the solid with the clean water, and then drying the product to obtain 159 kg of 3,5-dinitro-2-methylbenzoic acid, wherein the yield is 95.6% and the content is 98.7%, wherein 3000 kg of collected wastewater are needed to be treated.

Comparison 2

Adding 500 kg of the concentrated sulfuric acid in the 1000 L enamel reactor 12, starting the mixer 18, and then putting 100 kg of the ortho-toluic acid; after fully blended, adding 150 kg of the concentrated nitric acid, wherein the concentrated nitric acid completely added within 1 h by controlling the adding speed and the reaction temperature is controlled at not more than 100 DEG C.; keeping the reaction temperature for 40 min after the concentrated nitric acid is added completely; putting the cooled mixture into the diluting pot 13 in which 1200 kg of the recycled water is placed, and then mixing to dilute; filtering the fully cooled liquid, washing the solid with the clean water, and then drying the product to obtain 158 kg of 3,5-dinitro-2-methylbenzoic acid, wherein the yield is 95.1% and the content is 98%, wherein 2900 kg of collected wastewater are needed to be treated.

The device for recycling the waste acid produced in the process of producing the Zoalene, comprising an enamel reactor 12, wherein a mixer 18 is arranged in the enamel reactor 12, the enamel reactor 12 is provided with a nitric acid inlet 9, a sulfuric acid inlet 10 and an ortho-toluic acid inlet 11, wherein the outlet of the enamel reactor 12 is connected with a diluting pot 13, and the diluting pot 13 is connected with a filtering slot 14; the waste acid outlet 14 is connected with the distillation tower 1, the distillation tower 1 is connected with a vacuum pump 16, the acid liquid A outlet of the distillation tower 1 is connected with an acid liquid A storage tank 6, the acid liquid A storage tank 6 is connected with the inlet of a blending tank 8, the blending tank 8 is further connected with a concentrated sulfuric acid storage tank 4, the outlet of the blending tank 8 is connected with the sulfuric acid inlet 10 of the enamel reactor 12, the distilled water outlet of the distillation tower 1 is connected with a condenser 15, the outlet of the condenser 15 is connected with a recycled water storage tank 17, and the outlet of the recycled water storage tank 17 is connected with the diluting pot 13. As the further improving measure in the invention, for the device, the metering pump I 3 is arranged between the nitric acid storage tank 2 and the enamel reactor 12, and the metering pump I is used for controlling the required quantity of the nitric acid participating in reaction; the metering pump II 5 is arranged between the concentrated sulfuric acid storage tank 4 and the blending tank 8, and the metering pump II is used for controlling the required quantity of new sulfuric acid to be mixed; the metering pump III 7 is arranged between the acid liquid A storage tank 6 and the blending tank 8, and the metering pump III is used for controlling the required quantity of the acid liquid A to be mixed.

The product yield of the waste acid recycled in the invention is approximate to that of the product obtained in the production carried out with new concentrated sulfuric acid; therefore, not only the product quality is guaranteed, but also the discharge of the waste acid is reduced, environment is protected, and it is of great significance in production and living.

The embodiments in the invention are described in detail according to attachments and a large amount of experimental data, but the invention is not limited to the data; for ordinary technicians of the field, the technical scheme in the invention can be rationally changed in the condition of undeviating from the essential spiritual and the scope of the invention.

What is claimed is:

1. A process for recycling waste acid produced in the process of producing Zoalene, comprising a nitration process, a chlorination process and an ammonization process, wherein the nitration process comprises the following steps: putting concentrated sulfuric acid into an enamel reactor (12), starting a mixer (18), putting in ortho-toluic acid and mixing it until completely dissolved, adding nitric acid to the system, controlling the system temperature at 90-100 DEG. C., continuously mixing to react for 0.5-1.5 h after added, and then cooling; diluting the liquid with distilled water, then filtering, and then washing and drying the solid to obtain a nitration product 3,5-dinitro-2-methylbenzoic acid; putting the waste acid which is diluted and washed in the nitration process into a distillation tower (1), later heating, depressurizing and distilling; setting the vacuum degree for depressurizing and distilling the water acid at 0.07-0.1 MPa, putting the acid liquid A obtained by distillation and concentration into a mixing tank (8), and adding new concentrated sulfuric acid to the mixing tank (8), wherein the mass ratio of the acid liquid A to the new concentrated sulfuric acid mixed above is 1-5:1; after mixing, putting the mixed sulfuric acid to a reactor to carry out a new nitration reaction; recycling and putting the distilled water A which is obtained by heating, depressurizing and distilling into a condenser (15) for cooling, storing the cooled distilled water A in a recycled water storage tank (17), and putting the distilled water A to a diluting pot (13) to dilute the 3,5-dinitro-2-methylbenzoic acid produced in the new nitration process.

2. The process for recycling the waste acid produced in the process of producing the Zoalene according to claim 1, wherein the starting temperature to heat the waste acid is 50-120 DEG C., and the temperature to stop depressurizing and distilling the waste acid is 135-180 DEG C.

3. The process for recycling the waste acid produced in the process of producing the Zoalene according to claim 2, wherein the starting temperature to heat the waste acid is 90-110 DEG C., and the temperature to stop depressurizing and distilling the waste acid is 150-170 DEG C.

4. The process for recycling the waste acid produced in the process of producing the Zoalene according to claim 1, wherein the waste acid A and the new concentrated sulfuric acid are mixed and put in proportion of 2 to 3:1 by weight.

5. The process for recycling the waste acid produced in the process of producing the Zoalene according to claim 1, wherein the input rate of the added ortho-toluic acid:nitric acid:concentrated sulfuric acid is set as 1:2-3:5-18.

6. The process for recycling the waste acid produced in the process of producing the Zoalene according to claim 1, wherein the input rate of the added ortho-toluic acid:nitric acid:concentrated sulfuric acid is set as 1:2.2-2.6:8-12.

7. The process for recycling the waste acid produced in the process of producing the Zoalene according to claim 1, the dropping time of the nitric acid is 0.5-2 h.

8. A device for recycling the waste acid produced in the process of producing the Zoalene, comprising an enamel reactor (12), wherein a mixer (18) is arranged in the enamel reactor (12), the enamel reactor (12) is provided with a nitric acid inlet (9), a sulfuric acid inlet (10) and an ortho-toluic acid inlet (11), wherein the outlet of the enamel reactor (12) is connected with a diluting pot (13), and the diluting pot (13) is connected with a filtering slot (14); the waste acid outlet (14) is connected with the distillation tower (1), the distillation tower (1) is connected with a vacuum pump (16), the acid liquid A outlet of the distillation tower (1) is connected with an acid liquid A storage tank (6), the acid liquid A storage tank (6) is connected with the inlet of a blending tank (8), the blending tank (8) is further connected with a concentrated sulfuric acid storage tank (4), the outlet of the blending tank (8) is connected with the sulfuric acid inlet (10) of the enamel reactor (12), the distilled water outlet of the distillation tower (1) is connected with a condenser (15), the outlet of the condenser (15) is connected with a recycled water storage tank (17), and the outlet of the recycled water storage tank (17) is connected with the diluting pot (13).

9. The device according to claim 8, wherein a metering pump I (3) is arranged between a nitric acid storage tank (2) and the enamel reactor (12), a metering pump II (5) is arranged between the concentrated sulfuric acid storage tank (4) and the blending tank (8), and a metering pump III (7) is arranged between the acid liquid A storage tank (6) and the blending tank (8).

\* \* \* \* \*